United States Patent [19]

Pozuelo

[11] 4,117,161
[45] Sep. 26, 1978

[54] METHOD OF PHARMACOLOGICALLY TREATING DRUG ADDICTION WITH ALPHA-METHYL-PARA-TYROSINE

[76] Inventor: Jose Pozuelo, 1463 Burlington, Cleveland Hts., Ohio 44118

[21] Appl. No.: 797,372

[22] Filed: May 16, 1977

[51] Int. Cl.² ............................................ A61K 31/195
[52] U.S. Cl. .................................................... 424/319
[58] Field of Search .......................................... 424/319

[56] References Cited

U.S. PATENT DOCUMENTS 3,787,581  1/1974  Sandler ................................. 424/319

Primary Examiner—Stanley J. Friedman
Attorney, Agent, or Firm—Fay & Sharpe

[57] ABSTRACT

A method of pharmacologically alleviating craving for and withdrawal from narcotics and amphetamines in human beings which method comprises administering to a human being a therapeutically effective amount of alpha-methyl-para-tyrosine and an alkalinizing agent, with the alkalinizing agent being present in an amount sufficient to cause the urine of the human being to have an alkaline pH. Pharmaceutical compositions adapted for use in the foregoing method are also provided.

12 Claims, No Drawings

METHOD OF PHARMACOLOGICALLY TREATING DRUG ADDICTION WITH ALPHA-METHYL-PARA-TYROSINE

BACKGROUND OF THE INVENTION

The present invention relates to a method of overcoming the problems associated with treating patients who are addicted to narcotics and/or amphetamines. More specifically, it relates to a means of pharmacologically abolishing the craving and withdrawal syndrome normally experienced when a patient is deprived of such narcotics and/or amphetamines.

As above noted, two major aspects of the treatment of the individual drug addict relate to abolishing the craving and dependence, be they psychological or physical, and to the prevention of the withdrawal or abstinence snydrome. Attempts to accomplish these objectives in a pharmacological manner can be considered in two major categories: the replacement of the offending drug with one more acceptable, although still addictive, and the use of compounds that may alter the biochemical basis of addiction and withdrawal symptoms.

Previous experimental work in morphine addicted monkeys has demonstrated that treatment with alpha-methyl-para-tyrosine abolished the craving for morphine and diminished or abolished the manifestations of the abstinence syndrome. When the results of this investigation were first made known it was suggested that alpha-methyl-para-tyrosine could be used in the treatment of narcotic and amphetamine addictions and other mental conditions where the catecholamines were known to play a fundamental role.

The encouraging results of these experiments led, in 1972, to the trial of alpha-methyl-para-tyrosine in patients addicted to morphine. Unfortunately, they all developed alpha-methyl-para-tyrosine crystalluria, as in retrospect, had the monkeys, and treatment with this compound was discontinued.

Accordingly, the main object of the present invention is to provide a method of using alpha-methyl-para-tyrosine in the treatment of patients suffering from addiction to narcotics and/or amphetamines without the formation of alpha-methyl-para-tyrosine crystalluria.

Another object of the present invention is to provide a composition which is especially adapted to be used in the above-described method.

Other objects will be apparent to those skilled in the art from a reading of the following description and claims.

SUMMARY OF THE INVENTION

The present invention provides a safe and effective method of alleviating the craving and withdrawal syndrome associated with the treatment of persons addicted to narcotics and/or amphetamines. Broadly, this is accomplished by administering to an addicted person a therapeutically effective amount of alpha-methyl-meta-tyrosine and an alkalizing agent, with the alkalinizing agent being present in an amount sufficient to cause the urine of the person being treated to have an alkaline pH, preferably in excess of about 7.4.

In another apsect, the present invention concerns a pharmaceutical composition which is used in the practice of the foregoing method. This composition comprises a mixture of alpha-methyl-para-tyrosine and an alkalinizing agent.

A still further object of the invention is to provide a method of treating a human being with alpha-methyl-para-tyrosine while avoiding alpha-methyl-para-tyrosine crystalluria.

DESCRIPTION OF THE PREFERRED EMBODIMENTS OF THE INVENTION

The present invention concerns the use of alpha-methyl-para-tyrosine ($C_{10}H_{13}NO_3$) in the treatment of narcotic and/or amphetamine addiction. This compound is sometimes herein identified as AMPT. It has the following structural formula:

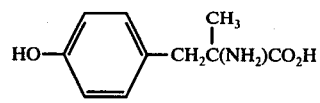

In the practice of the present invention alpha-methyl-para-tyrosine is administered in a therapeutic amount. That is, the person being treated is given increasing amounts of the concerned compound until the craving and the withdrawal syndrome is no longer observed. The exact amount to be utilized varies from person to person depending on the degree of addiction and is determined emperically. However, in practice alpha-methyl-para-tyrosine is usually administered in amounts ranging from about 100 to about 250 milligrams per kilogram of body weight per day.

The alkalinizing agent can be any one of the many materials used to alkalinize urine. Such materials include, but are not limited to, sodium bicarbonate, ammonium chloride, and the like. An alkalinizing agent which is especially effective is a commercially available product known as Polycitra, manufactured by Willen Drug Company. This product contains 30 grains of citric acid, 45 grains of sodium citrate and 50 grains of potassium citrate for every 30 ml of syrup base solution.

The exact amount of alkalinizing agent to be utilized varies from person to person and the diet the individual receives. All that is required is that sufficient alkalinizer be utilized to render the urine of the person being treated basic. However, it is preferred that the pH of the urine of the person being treated must be greater than about 7.4 in order to prevent alpha-methyl-para-tyrosine crystalluria. In practice, it has been determined that it is most desirable to use enough alkalinizer to cause the urine of the person being treated to exhibit a pH of about 7.8 to 8.0 (ideal).

The alpha-methyl-para-tyrosine can be administered in various ways. For example, it can be given in pill or capsule form, with or without a filler, along or together with an alkalinizing agent. If desired, it can be administered intravenously. In such a case, it is convenient to dissolve the alpha-methyl-para-tyrosine in a basic solvent. This is readily accomplished by mixing the powered compound with a buffer phosphate solution (500 mg of AMPT and 10 ml buffer phosphate) and dissolving it at a pH of 11.5 by adding NaOH and bringing the pH to 7.4 to 8 with HCl solution. The compound solution is then diluted further in sterile water to obtain 500 ml of solution, correcting the final pH to 7.4.

As above note, the alpha-methyl-para-tyrosine, or the alkalinizing agent or the combination thereof can be mixed with other materials. For example, in the case of a tablet, the composition can also include, fillers, binders, and diluents such as lactose, methylcellulose, talc, gum tragancanth, gum acacia, agar, polyvinylpyrrolidone, calcium stearate, and/or corn starch, etc. In the case of a liquid solution or suspension for oral administration, the composition can include, a filler such as sodium carboxymethylcellulose and/or syrup, e.g., a glycerine based syrup. In the case of a parenteral solution or suspension, the composition will comprise, a suitable solvent or other liquid such as a saline solution.

The practice of the present invention is further exemplified by the following general discussion and case studies.

All patients with well documented histories of addiction and dependence on various narcotics and/or amphetamines. All patients submitted voluntarily to the study designed to show the effectiveness of the present invention. All patients had severe, chronic amphetamine or narcotic addiction.

The narcotic dependent patients were transferred from the irregular doses of heroin or other substitutes they could obtain to satisfy their craving and prevent the manifestations of abstinence was established. A period of a week was used for each patient; not only to confirm the morphine requirement, but also to study catecholamine levels, urinary pH, and other constants. During this initial week, the patients assigned to be treated with AMPT were carefully studied to determine the requirements to obtain a urinary pH close to 8.

Doses of AMPT were started after the baseline was determined, and increased gradually until either a therapeutic level was reached, as measured by the lack of desire of the patient to have narcotics or amphetamines, or previously established maximum serum levels of AMPT were reached. Having established the tentative doses of the alkalinizer Polycitra to obtain a urinary pH close to 8, the patients to be treated with AMPT were started on a dose of 50 mg/kg of body weight per day which was increased gradually at the rate of 25 mg/kg of body weight every 2 days.

Urine specimens were checked four times daily on patients receiving AMPT to determine the urinary pH and to look for crystals of AMPT in the sediment.

The morphine addicted patients were maintained on regular doses of morphine, and amphetamine dependent patients on 40 to 60 mg amphetamine per day to prevent a rebound of amphetamine depression.

When the dosage of AMPT administered orally was close to 80 mg/kg of body weight for the narcotic group of patients, the regular dosage of morphine was discontinued and given only at the patient's request. For the amphetamine dependent patients, amphetamines were discontinued after reaching a dose of 100 mg AMPT/kg/day, the patients being told that the amphetamines would be given if they still craved them.

Case Reports

Case 1. A 30-year-old housewife, married 12 years and mother of four children, seemed to be a stable person, free of neurotic traits. She had started to take a combination of dextroamphetamine and dihydrochlorothiazide (dihydrodiuril) 7 years before because of overweight after her second pregnancy and delivery. Increased doses of dextroamphetamine were required to overcome fatique. When she entered this study, she was taking about 150 mg of dextroamphetamine and 200 mg of dihydrochlorothiazide daily in addition to eight to 10 tablets containing aspirin, codeine and phenobarbital for relief of severe headaches. Without use of these drugs she could not prepare breakfast nor take her children to school. She would continue taking 30 to 40 mg dextroamphetamine every 3 to 4 hours. Each day she stopped taking amphetamines about 6 P.M. so that fatigue and exhaustion would allow her to sleep without sedatives. After baseline studies were completed the patient was given AMPT and the urine was alkalinized to a pH close to 8. Doses of 8 grams AMPT a day were sufficient to suppress the craving for amphetamines and to abolish the fatigue and withdrawal manifestations.

The patient remained in the hospital for four weeks and was discharged 19 days after initiation of AMPT treatment. Amphetamines prescribed at first regularly were withdrawn and given only at the request of the patient after reaching a daily dose of 7 grams AMPT. She never requested amphetamines again. This patient reported no need for amphetamines on discharge and remembered with "nausea and rage" the need for the amphetamines because of the many troubles she had had with them.

Case 2. A 24-year-old married man had started to experiment with marijuana and LSD 4 to 5 years before. He started to take cocaine and heroin 3 years ago and had regular periods each month during which he "mainlined" 1 gram of heroin a day. When heroin was not available or available only in lesser amounts than needed, other substitutes such as trilitrate were use.

To compensate his heroin dependence with morphine, about 300 mg of morphine was needed daily in four to six divided doses to satisfy his craving and prevent the initiation of withdrawal between doses. He was started on AMPT, 3 grams per day, and the dosage was increased gradually to a maximum of 11 grams per day, in four divided doses. The requirements for morphine, always available to the patient at his request, decreased gradually after the dosage of AMPT reached 8 grams per day. Morphine was requested at longer spaced intervals and for lower amounts each time. The pH of the urine was maintained close to 8 by administration of the urinary alkalinizer Polycitra. The patient stopped requesting morphine on the 8th day of AMPT treatment, when he was receiving 10 grams AMPT per day in four divided doses. He was maintained on 6 grams AMPT per day for another 17 days.

When discharged from the hospital after receiving AMPT treatment for 25 days, he stated that he had no craving for heroin nor any manifestations of withdrawal, signs of which were very well known to this knowledgeable patient. He neither craves morphine nor has had any manifestations of withdrawal symptoms since he left the hospital.

Case 3. A 23-year-old married woman had many family conflicts and neurotic traits, being a "nervous child" for as long as she could remember.

She started to smoke marijuana and sniffed cocaine for about 6 years. She also took LSD and barbiturates. However, for the past 3 to 4 years she has consumed heroin and cocaine almost exclusively, and had it available most of the time. She use pentazocine when heroin was not available, "mainlining" it to the "rhythm" of 25 to 30 injections per day (750–900 mg). To compensate for her dependence on narcotics she needed about 300 mg morphine a day, in four to six divided doses.

She was given an initial dose of 3 grams AMPT per day and the dosage was gradually increases to a maximum of 10 grams a day, in four divided doses. Meanwhile, her urine was alkalinized to a pH close to 8; the pH was checked four times daily and the urine specimens were examined for crystalluria. The patient gradually reduced her requests for morphine and stopped taking it on the 15th day of AMPT treatment when the dosage was 10 grams daily.

After the above treatment, the patient stopped craving for drugs and did not manifest any withdrawal symptoms.

Case 4. A 28-year-old, married man, a polyaddict for 3 to 4 years, had resorted to the heavy use of cocaine and heroin. Because this patient did not follow the established protocol he was formally excluded from the study. However, before he admitted to violating the protocol, he had stopped taking morphine when receiving 10 grams AMPT daily in four divided doses. He was later returned to the study and again responded to 10 grams AMPT with no desire for morphine and no evidence of withdrawal.

None of the patients receiving AMPT have had crystals in any daily urine specimen. Except for a slight drowsiness no side effects have been observed and the patients deny any signs of intolerance. Hypotension was observed in two patients but was mild and never causes dizziness nor prevented them from normal activity.

Numerous other patients addicted to such drugs as amphetamines, heroin, pure morphine, methadone, pentazocine have also been treated in accordance with the teachings of the present invention. All such patients were free from craving or withdrawal symptoms and none experienced AMPT crystalluria.

The results and information set forth above indicate that alpha-methyl-para-tyrosine is effective in abolishing the craving for morphine and amphetamines, and in preventing manifestations of withdrawal in human addicts. The fact that the morphine and amphetamines were readily available at the patients' requests and that the patients rejected them because the craving had disappeared, and there were no manifestations of withdrawal lends further support to the study.

The effects of alpha-methyl-para-tyrosine are thought to be due, in the main, to the inhibition of catecholamine synthesis and consequent decreased content of catecholamines in the brain. However, the present invention is not necessarily directed to this mechanism but to a means for alleviating craving and withdrawal syndromes experienced by narcotic and amphetamines addicts.

In fact, one additional aspect of the present invention is the provision of a means for using alpha-methyl-para-tyrosine in human beings without experiencing crystalluria, regardless of the exact condition being treated. As before noted in detail, this is accomplished by concurrently administering to the person taking AMPT a sufficient amount of alkalinizer to cause the patient's urine to be basic, preferably with a pH about 7.4. In this regard, it is to be noted that by using the broad concept of the present invention it is possible to treat mental patients suffering from schizophrenia and manic psychosis with alpha-methyl-para-tyrosine.

While there have been described what are at present considered to be the preferred embodiments of this invention, it will be obvious to those skilled in the art that various changes and modifications may be made therein without departing from the invention, and it is, therefore, aimed in the appended claims to cover all such changes and modifications as fall within the true spirit and scope of the invention.

What is claimed is:

1. A method of preventing alpha-methyl-para-tyrosine crystalluria in a human being who is being treated with a therapeutically effective amount of alpha-methyl-para-tyrosine, comprising:
    administering to said human being treated with alpha-methyl-para-tyrosine an alkalinizing agent in an amount sufficient to cause the urine of said human being to have an alkaline pH.

2. The method of claim 1 wherein said alkalininzing agent is present in an amount sufficient to cause the pH of said urine to be in excess of about 7.4.

3. The method of claim 1 wherein alkalinizing agent is used in an amount sufficient to cause the pH of said urine to range from about 7.8 to 8.0.

4. The method of claim 1 wherein said alkalinizing agent is selected from the group consisting of sodium bicarbonate, ammonium chloride and mixtures thereof.

5. The method of claim 1 wherein said alkalinizing agent is a mixture of citric acid, sodium citrate and potassium citrate.

6. The method of claim 1 wherein said alpha-methyl-para-tyrosine is administered in an amount ranging from about 100 to about 250 mg/kg of body weight.

7. A pharmacological method of alleviating craving for and withdrawal from narcotics and amphetamines without the formation of alpha-methyl-para-tyrosine crystalluria in human beings said method comprising:
    administering to an addicted human being a therapeutically effective amount of alpha-methyl-para-tyrosine and an alkalinizing agent, said alkalinizing agent being present in an amount sufficient to cause the urine of said human being to have an alkaline pH.

8. The method of claim 7 wherein said alkalinizing agent is present in an amount sufficient to cause the pH of said urine to be in excess of about 7.4.

9. The method of claim 8 wherein alkalinizing agent is used in an amount sufficient to cause the pH of said urine to range from about 7.8 to 8.0.

10. The method of claim 7 wherein said alkalinizing agent is selected from the group consisting of sodium bicarbonate, ammonium chloride and mixtures thereof.

11. The method of claim 7 wherein said alkalinizing agent is a mixture of citric acid, sodium citrate and potassium citrate.

12. The method of claim 7 wherein said alpha-methyl-para-tyrosine is administered in an amount ranging from 100 to about 250 mg/kg of body weight.

* * * * *